United States Patent [19]

Kikuchi et al.

[11] Patent Number: 5,166,363
[45] Date of Patent: Nov. 24, 1992

[54] PROCESS FOR PRODUCING 1,3-BIS(DICARBOXYPHENYL)-DISILOXANE DERIVATIVE OR DIANHYDRIDE THEREOF

[75] Inventors: Tohru Kikuchi; Toshiyuki Fujita; Koichi Kamijima; Takayuki Saito, all of Hitachi, Japan

[73] Assignee: Hitachi Chemical Company, Ltd., Tokyo, Japan

[21] Appl. No.: 803,897

[22] Filed: Dec. 9, 1991

Related U.S. Application Data

[63] Continuation of Ser. No. 491,828, Mar. 12, 1990, abandoned, which is a continuation-in-part of Ser. No. 194,346, May 16, 1988, abandoned.

[30] Foreign Application Priority Data

May 19, 1987 [JP] Japan .................. 62-121546
Jun. 18, 1987 [JP] Japan .................. 62-152199

[51] Int. Cl.$^5$ ........................... C07F 7/07; C07F 7/20
[52] U.S. Cl. ........................... 549/214; 556/453; 556/463
[58] Field of Search ............... 549/214; 556/453, 463

[56] References Cited

U.S. PATENT DOCUMENTS

| | | | |
|---|---|---|---|
| 2,458,944 | 1/1949 | Hyde .................. | 556/453 |
| 2,891,981 | 6/1959 | Gainer et al. .......... | 260/448.2 |
| 3,328,448 | 6/1967 | Barnes et al. .......... | 556/463 |
| 4,542,226 | 9/1985 | Eddy et al. ............ | 549/214 |

FOREIGN PATENT DOCUMENTS

243028A1 2/1987 Fed. Rep. of Germany ...... 556/453
981824 1/1965 United Kingdom .

OTHER PUBLICATIONS

Journal of Organic Chemistry, vol. 38, No. 25, 1973, pp. 4271-4274; J. R. Pratt et al.
Houben-Weyl: "Methoden de organischen Chemie" vol. XIII/5, edition 4, 1980, pp. 34, 45-50, 132-133, 140-141.
Helvetica Chimica Acta, vol. 57, No. 110, fasc. 4, Jun. 5, 1974 pp. 1010-1015.
McMurry, John; "Organic Chemistry", p. 776, Chapter 24, Brooks/Cole Co., USA 1984.

*Primary Examiner*—C. Warren Ivy
*Assistant Examiner*—Ba K. Trinh
*Attorney, Agent, or Firm*—Antonelli, Terry, Stout & Kraus

[57] ABSTRACT

A process for producing (i) a 1,3-bis(dicarboxyphenyl)-disiloxane derivative represented by the general formula

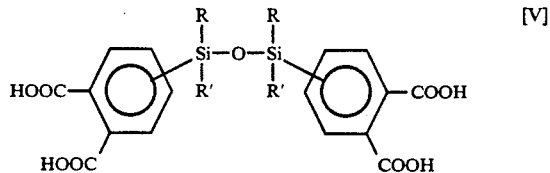

wherein Rs and R's independently of one another denote methyl or phenyl or (ii) a 1,3-bis(dicarboxyphenyl)-disiloxane derivative dianhydride represented by the general formula

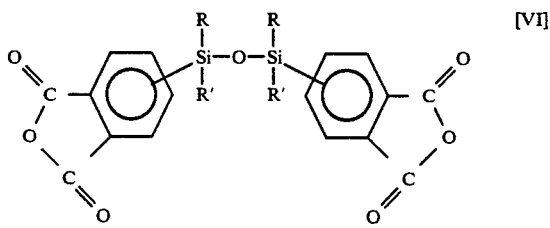

wherein Rs and R's are as defined above, the process comprising
coupling a Grignard reagent of halo-o-xylene with a disubstituted halosilane represented by the general formula

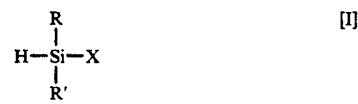

wherein R and R' are as defined above and X denotes halogen, to form a dimethylphenyl(disubstituted silane) represented by the general formula

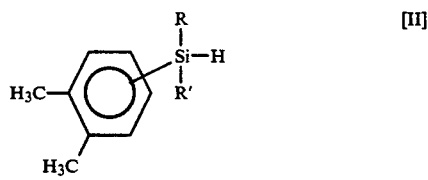

wherein R and R' are as defined above,
hydroxylating the dimethylphenyl(disubstituted silane) to form a dimethylphenyl(disubstituted hydroxysilane) represented by the general formula

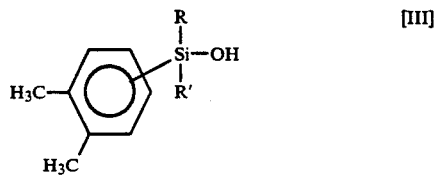

(Abstract continued on next page.)

wherein R and R' are as defined above, to form a 1,3-bis(dimethylphenyl)-disilane dehydrating-condensing the dimethylphenyl-(disubstituted hydroxysilane derivative represented by the general formula

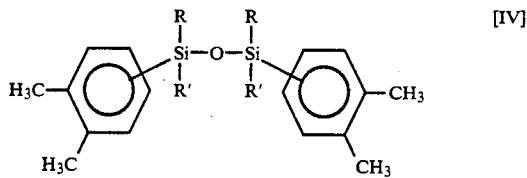

wherein Rs and R's are as defined above, and oxidizing the 1,3-bis(dimethylphenyl)disilane derivative to yield the intended 1,3-bis(dicarboxyphenyl)-disiloxane derivative of general formula [V], or further comprising the dehydration ring closure of this product to form a 1,3-bis(dicarboxyphenyl)-disiloxane derivative dianhydride of general formula [VI], mixing the resulting isomeric mixture with an ether solvent, and recovering the formed precipitate to yield a white powder of the intended product of general formula [VI].

8 Claims, No Drawings

PROCESS FOR PRODUCING 1,3-BIS(DICARBOXYPHENYL)-DISILOXANE DERIVATIVE OR DIANHYDRIDE THEREOF

This application is a continuation application of application Ser. No. 491,828, filed Mar. 12, 1990, now abandoned which is a continuation application of application Ser. No. 194,346, filed May 16, 1988 (now abandoned).

BACKGROUND OF THE INVENTION

1. Field of the Invention

The present invention relates to a process for producing 1,3-bis(dicarboxyphenyl)disiloxane derivatives or dianhydrides thereof which are useful as raw materials of polyimide resins, as hardeners for epoxy resins, and as others.

2. Description of the Prior Art

Of the 1,3-bis(dicarboxyphenyl)disiloxane derivatives represented by the general formula [V],

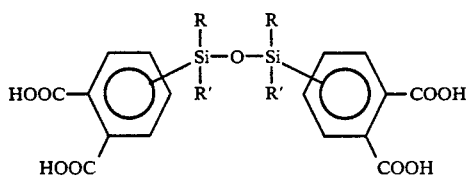

wherein, Rs and R's independently of one another denote methyl or phenyl, a compound having methyl groups as Rs and R's and containing carboxy groups at the 3- and 4-positions of each phenyl group, viz. 1,3-bis(3,4-dicarboxyphenyl)-1,1,3,3-tetramethyldisiloxane represented by the formula [VII],

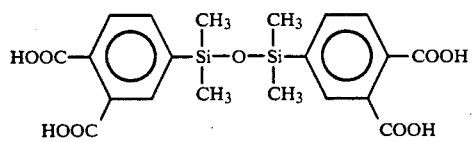

can be synthesized by a known process described in J. Org. Chem., Vol. 38, p. 4271 (1973). This synthetic process is based on the following reaction scheme [VIII]:

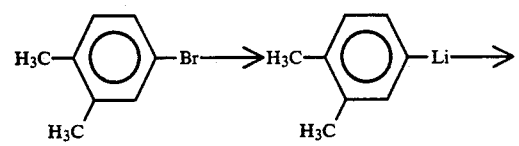

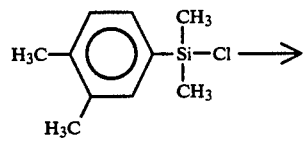

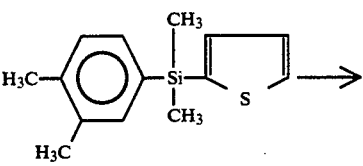

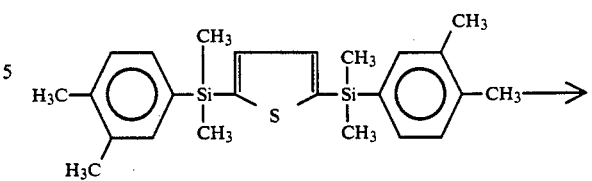

Compound of formula [VII]

That is, the process comprises reacting 4-bromo-o-xylene with n-butyllithium, reacting the resulting lithium compound with dichlorodimethylsilane, reacting the resulting dimethyl (3,4-dimethylphenyl)-chlorosilane with thiophene, reacting the resulting 2-(3,4-dimethylphenyldimethylsilyl) thiophene with dimethyl (3,4-dimethylphenyl)chlorosilane, oxidizing the resulting 2,5-bis(3,4-dimethylphenyldimethylsilyl)-thiophene with potassium permanganate, and acidifying the resulting aqueous solution of potassium carboxylate to precipitate and recover the intended tetracarboxylic acid of formula [VII]. Said paper also describes the method of treating with acetic anhydride during the reaction and reports that the melting point of the thus obtained dianhydride represented by the formula [XII],

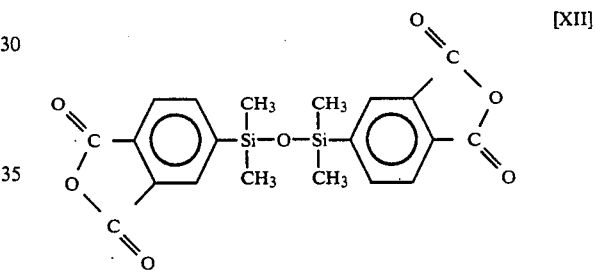

was found to be 137°–138° C.

A process based on the reaction scheme [IX]:

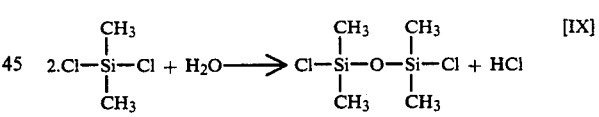

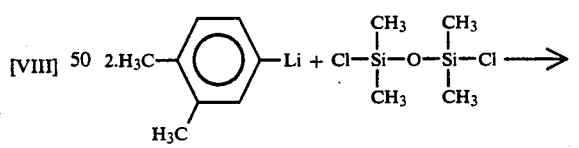

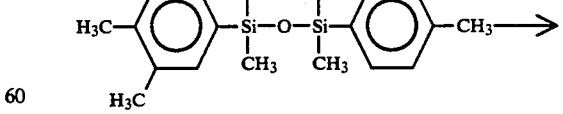

Compound of formula [VII]

is described in "polyimides", Vol. 1, p. 51, edited by K. L. Mittal, published by Plenum Press. That is, the process comprises hydrolyzing dichlorodimethylsilane, reacting the resulting 1,3-dichlorotetramethyldisiloxane with a lithium compound which is the reaction product of 4-bromo-o-xylene and n-butyllithium, oxidizing the resulting 1,3-bis(3,4-dimethylphenyl)-1,1,3,3-tetramethyldisiloxane with potassium permanganate, and acidifying the resulting aqueous solution of potassium tetracarboxylate to precipitate and recover the intended tetracarboxylic acid of formula [VII]. The "Polyimides", Vol. 1 further reports that recrystallization from n-hexane gave a dianhydride of formula [XII] having a melting point range of 156°–159° C.

Japanese Patent Application Laid-Open No. 83191/86 describes another process based on the following reaction scheme [X]:

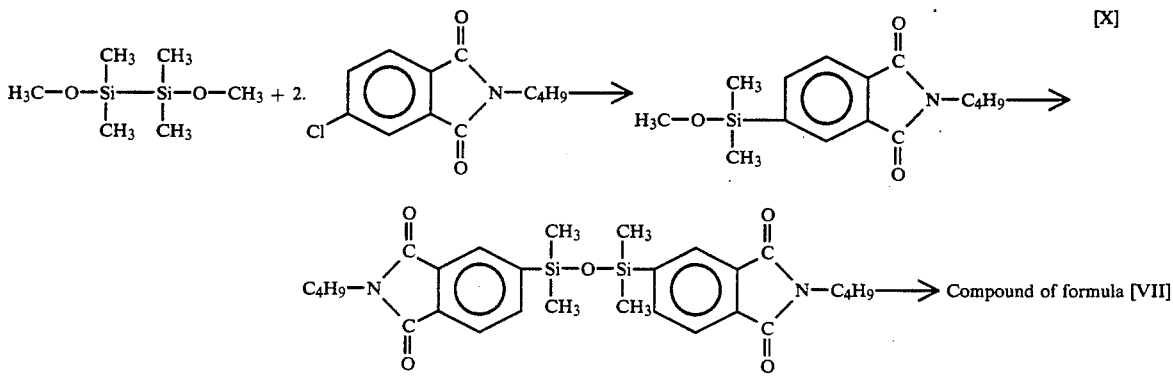

That is, the process comprises reacting 1,2-dimethoxytetramethyldisilane with N-n-butyl-4-chlorophthalimide, hydrolyzing the resulting 4-(dimethylmethoxysilyl)-N-n-butylphthalimide, followed by alkalihydrolysis of the resulting bisphthalimide compound of disiloxane to give the product tetracarboxylic acid.

All the above described prior art processes, however, have the disadvantages of many reaction steps required and low yields of intermediates and one of these processes employs a special compound as a raw material.

That is, in the process described in J. Org. Chem., based on reaction scheme [VIII], the yield of dimethyl(3,4-dimethylphenyl)chlorosilane, which is an intermediate, is as low as 56%, while the yield of the end product of formula [VII] is uncertain (the yield is not described). In this process, the phthalic anhydride groups of the compound of formula [XII] is derived from 4-bromo-o-xylene. However, industrial synthetic processes provide 4-bromo-o-xylene contaminated with about 25% by weight of 3-bromo-o-xylene, such mixtures only being available. In consequence, when the synthesis of the dianhydride of formula [XII] is tried by using such a mixture of 4-bromo-o-xylene and 3-bromo-o-xylene, the silicon-containing tetracarboxylic dianhydride only obtained is a mixture composed of isomers represented by the general formula [XI],

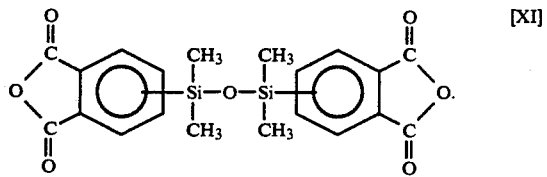

When this isomeric mixture is used as the raw material of a polyimide resin, the resulting resin has a low degree of polymerization and is inferior in heat resistance. In order to solve this problem, the dianhydride of formula [XII] should be separated from the isomeric mixture and purified before use as the raw material of a polyimide.

The present inventors also tried the separation and purification by using each of acetic anhydride and n-hexane as stated above, finding the following problems.

The product yield from the purification with acetic anhydride was very low since the isomeric mixture is highly soluble in acetic anhydride.

The recrystallization from n-hexane was found to need a vast volume of n-hexane because the dianhydride of formula [XII] is scarcely soluble in n-hexane.

According to the process based on the reaction scheme [IX], described in "Polyimides" edited by K. L. Mittal, 1,3-dichlorotetramethyldisiloxane is obtained as an intermediate by hydrolysis of dichlorodimethylsilane that is a fundamental compound in silicon chemistry. In this case, however, polysiloxane compounds such as 1,5-dichlorohexamethyltrisiloxane are produced incidentally and the yield of 1,3-dichlorotetramethyldisiloxane is only 22%. Moreover, 1,3-bis(3,4-dimethylphenyl)-1,1,3,3-tetramethyldisiloxane is obtained but in a low yield of 36% by the double cross coupling of the 1,3-dichlorotetramethyldisiloxane with a lithium compound. Furthermore, since 4-bromo-o-xylene is also used in this process, only a mixture of isomers represented by general formula [XI] can be obtained as in the process described in J. Org. Chem., Vol. 38.

According to the process based on the reaction scheme [X], described in Japanese Patent Application Laid-Open No. 83191/86, 4-(dimethylmethoxysilyl)-N-n-butylphthalimide is obtained by reacting N-n-butyl-4-chlorophthalimide with 1,2-dimethoxytetramethyldisilane under toluene reflux in the presence of a palladium catalyst, but the disilane compound used in this case is a quite special compound expensive and dangerous in that spontaneous ignition thereof takes place in the air. This compound is used as much as four times the theoretical amount for the reaction. Although the yield of intermediate 4-(dimethylmethoxysilyl)-N-n-butylphthalimide is reported to be 83% on the basis of N-n-butyl-4-chlorophthalimide, no description is given about the yield of the bisphthalimide of disiloxane produced in the next step and only the possibility of production is set forth about the compound of formula [VII].

As described above, no industrial process has been established for producing the silicon-containing tetracarboxylic acid of formula [VII], those of general formula [V], or the dianhydride of formula [XII].

SUMMARY OF THE INVENTION

The present invention involves a process for producing (i) a 1,3-bis(dicarboxyphenyl)disiloxane derivative represented by the general formula

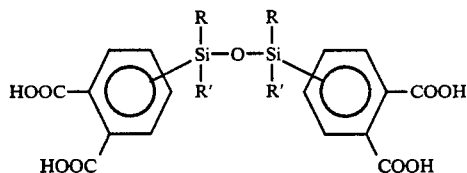

wherein Rs and R's independently of one another denote methyl or phenyl or (ii) a 1,3-bis(dicarboxyphenyl)-disiloxane derivative dianhydride represented by the general formula

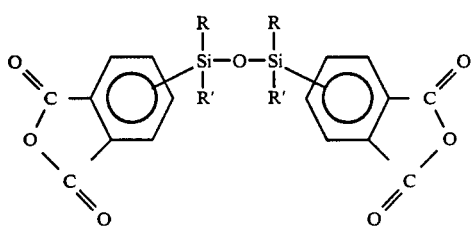

wherein Rs and R's are as defined above, the process comprising coupling a Grignard reagent of halo-o-xylene with a disubstituted halosilane represented by the general formula

wherein, R and R' are as defined above and X denotes halogen, to form a dimethylphenyl(disubstituted silane) represented by the general formula [II],

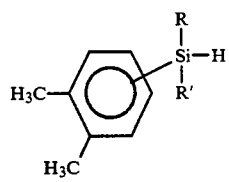

wherein R and R' are as defined above, hydroxylating the dimethylphenyl-(disubstituted silane) to form a dimethylphenyl-(disubstituted hydroxysilane) represented by the general formula [III],

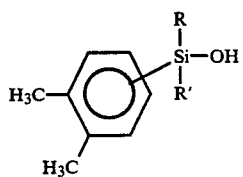

wherein R and R' are as defined above, dehydrating-condensing the dimethylphenyl-(disubstituted hydroxysilane) to form a 1,3-bis-(dimethylphenyl)disiloxane derivative represented by the general formula [IV],

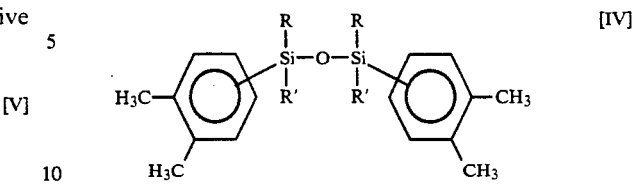

wherein Rs and R's are as defined above, and oxidizing the 1,3-bis(dimethylphenyl)disiloxane derivative to yield the intended 1,3-bis(dicarboxyphenyl)-disiloxane derivative of general formula [V],

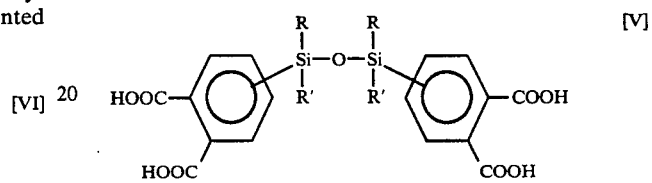

wherein Rs and R's are as defined above, or further comprising the dehydration ring closure of this product to yield the intended 1,3-bis-(dicarboxyphenyl)disiloxane derivative dianhydride of general formula [VI],

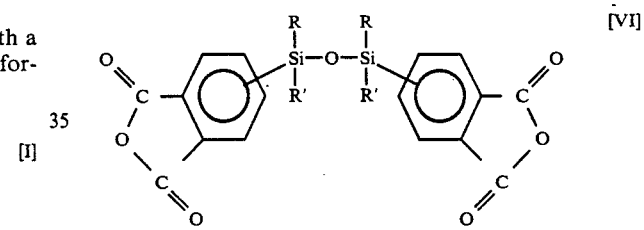

wherein Rs and R's are as defined above.

When the dianhydride of general formula [VI] is a mixture of isomers represented by general formula XI], the process additionally comprises mixing this isomeric mixture with an ether solvent, and recovering the formed precipitate to yield a white powder of the intended product of formula [XII].

DETAILED DESCRIPTION OF THE INVENTION

Hereinafter the production process of the present invention is described in detail.

Suitable halo-o-xylenes for use in the form of Grignard reagent in the production process include; 4-halo-o-xylenes, e.g. 4-iodo-o-xylene, 4-bromo-o-xylene, and 4-chloro-o-xylene; and 3-halo-o-xylenes, e.g. 3-iodo-o-xylene, 3-bromo-o-xylene, and 3-chloro-o-xylene. These compounds may be used alone or in combination.

The halo-o-xylene can be converted to the Grignard reagent thereof by the ordinary method. For instance, the Grignard reagent is prepared by using 1.0 gram atom or more of metallic magnesium per 1.0 mole of the halo-o-xylene. When the amount of metallic magnesium used is less than 1.0 gram atom, a part of the halo-o-xylene remains unreacted and in the step of coupling, it reacts with a part of the Grignard reagent to produce tetramethylbiphenyl, which is undesirable. The preparation of the Grignard reagent is carried out between 0°

C. and the reflux temperature of the used solvent for a period generally from 1 to 10 hours.

When the amount of metallic magnesium used exceeds 1.0 gram atom per 1.0 mole of the halo-o-xylene, unreacted metallic magnesium remains. This is removed by filtration. Suitable solvents for use in the reaction to prepare the Grignard reagent are ethyl ether, tetrahydrofuran, and the like.

Examples of the disubstituted halosilane to use in the first step of the present process include dimethylchlorosilane, dimethylbromosilane, diphenylchlorosilane, diphenylbromosilane, methylphenylchlorosilane, and methylphenylbromosilane. Addition of such a disubstituted halosilane to the Grignard reagent allows the coupling reaction to proceed.

The disubstituted halosilane is used desirably in an amount of 0.5 to 1.5 moles per 1.0 mole of the Grignard reagent of halo-o-xylene. When the amount is less than 0.5 mole, the yield of coupling product is too low and a large amount of Grignard reagent remains unreacted, but this is hydrolyzed by washing with water to convert to o-xylene, which does not disturb the following reaction.

When the amount of disubstituted halosilane exceeds 1.5 moles, after completion of the reaction, the remaining excess thereof converts into tetrasubstituted disiloxane compounds, which cause a side-reaction and contamination during the production of the intermediate compound of formula [IV]. This contaminant can be removed by distillation. For the purpose of offsetting this disadvantage, the disubstituted halosilane is used in an amount preferably from 0.9 to 1.1 moles, most desirably from 0.95 to 1.0 mole, per 1.0 mole of the Grignard reagent of halo-o-xylene.

The coupling reaction is carried out at a temperature desirably from 0° to 60° C. for a period generally from 1 to 5 hours. When the reaction temperature is low, the reaction period is prolonged but no fundamental problem arises. On the contrary, when the reaction temperature is higher than 60° C., the reaction compound vaporizes and dissipates under normal pressure. This is accompanied by a decrease in the yield. For the purpose of preventing this, it is advisable to use a pressurized reactor.

It is desirable to add water after completion of the coupling reaction, thereby decomposing the remaining Grignard reagent to o-xylene and simultaneously dissolving magnesium halide produced by the coupling, in the water to separate and eliminate the magnesium halide. This separation and elimination can be accomplished by withdrawing the lower aqueous layer from the upper organic layer (a solution in an organic solvent such as ethyl ether or tetrahydrofuran) which are formed in the reactor by the addition of water. Then, the organic layer, which contains a dimethylphenyl(disubstituted silane) of general formula [II], is preferably washed with water and once dehydrated before going to the next step. The dimethylphenyl(disubstituted silane) can be purified by distillation as occasion demands. However, the next step can be operated without conducting the wash, dehydration, and purification by distillation.

Subsequently, water and a palladium catalyst are added to the resulting solution of the dimethylphenyl(disubstituted silane) in an organic solvent such as ethyl ether or tetrahydrofuran to produce a dimethylphenyl(disubstituted hydroxysilane) of formula [III]. In this case, the amount of water to be added is desired to be 1.0 mole or more per 1.0 mole of the dimethylphenyl(disubstituted silane). Suitable palladium catalysts include; organic palladium compounds such as dichlorobis(triphenylphosphine)palladium and dichloro[1,2-bis(diphenylphosphino)ethane]palladium; so-called metallic palladium catalyst that is metallic palladium supported by a carrier such as active carbon or alumina; and palladium black. Desirably, the palladium catalyst is added in such an amount that the proportion of palladium metal to the dimethylphenyl(disubstituted silane) may be from 0.005 to 0.05% by weight. This reaction finishes in a period of 1 to 5 hours at temperatures of 10° to 50° C.

Since hydrogen gas is evolved by this reaction, the degree of reaction progress can be measured from the amount of this gas evolved. After completion of the reaction, the catalyst used is eliminated by filtration and the excess water is removed by means of a separating funnel, giving an organic layer containing the dimethylphenyl(disubstituted hydroxysilane). As occasion demands, the organic solvent that is ethyl ether or tetrahydrofuran is removed and the dimethylphenyl-(disubstituted hydroxysilane) can be purified by distillation. Ordinarily, however, the above organic solution obtained is subjected as such to the next dehydration-condensation reaction.

Then an acid catalyst is added to the organic solution to hydrate-condense the dimethylphenyl-(disubstituted hydroxysilane) to a 1,3-bis(dimethylphenyl)-disiloxane derivative of general formula [IV]. Useful acid catalysts include mineral acids, e.g. hydrochloric acid and sulfuric acid. Such an acid is used desirably in an amount of 0.05 to 1.0 mole per 1.0 mole of the dimethylphenyl(disubstituted hydroxysilane). The temperature of this reaction is desirably in the range of 10° to 40° C., where the reaction is complete in a period of 1 to 10 hours. When the reaction temperature exceeds 40° C., polysiloxane compounds are liable to form incidentally.

Upon stopping stirring after completion of the reaction, the reaction mixture separates into an upper organic layer consisting of a solution of the 1,3-bis-(dimethylphenyl)disiloxane derivative in an organic solvent such as ethyl ether or tetrahydrofuran and a lower aqueous layer consisting of the acid catalyst used and water produced by the reaction. The lower layer is removed, the upper layer is washed with water, and the organic solvent is distilled off to recover the 1,3-bis(dimethylphenyl)disiloxane derivative, which may be purified by distillation if necessary.

The product 1,3-bis(dicarboxyphenyl)disiloxane derivative that is a silicon-containing tetracarboxylic acid of general formula [V] can be obtained by oxidizing the above intermediate 1,3-bis(dimethylphenyl)disiloxane derivative.

For this reaction, it is possible to utilize a liquid-phase autooxidation which is oxidation with oxygen or air in the presence of an organic cobalt catalyst or an oxidation employing a permanganate.

The organic cobalt catalyst used in the liquid-phase autooxidation is such as cobalt naphthenate or cobalt octenate. The catalyst is used in an amount of 1 to 5 mole % based on the 1,3-bis(dimethylphenyl)-disiloxane derivative.

Suitable solvents for use in this reaction are aliphatic carboxylic acids such as acetic acid and propionic acid. The reaction is carried out at a temperature of 150° to 230° C. and a pressure of 5 to 50 kg/cm$^2$ by using additionally an alkali halide such as sodium bromide, sodium chloride, or potassium bromide in an amount of 1 to 5 mole % based on the above derivative. After completion of the reaction, a solvent such as toluene, ethyl ether, or isopropyl ether is added to extract the reaction product into the solvent layer, and this solvent layer is taken out and washed with water to remove the aliphatic carboxylic acid used as a reaction solvent and the co-catalyst. Then, the 1,3-bis(dicarboxyphenyl)disiloxane derivative can be obtained by distilling off the solvent used for extraction.

Potassium permanganate and other permangates can be used in the liquid-phase autooxidation. The solvent used in this case is a mixture of water and an organic solvent such as pyridine, dioxane, or t-butanol. The weight ratio of the organic solvent to water is desired to be 0.5-3.0:1.0. To 100 g of this water-organic solvent mixture are added 2-15 g of the 1,3-bis(dimethylphenyl)disiloxane derivative and then gradually potassium permanganate in a molar ratio of at least 12 to the derivative. When this molar ratio is less than 12, the oxidation yield is unsatisfactory. The reaction temperature is between 50° C. and the reflux temperature and the reaction period is generally from 5 to 10 hours. The potassium permanganate is converted by this reaction into manganese oxide, which, insoluble in the solvent mixture, is removed by filtration. Since the 1,3-bis(dicarboxyphenyl)disiloxane derivative in the form of potassium salt is dissolved in the filtrate that contains the above-mentioned organic solvent, the derivative is precipitated by adding concentrated hydrochloric acid after the organic solvent has been distilled off. The amount of conc. hydrochloric acid to add is such that the pH of the aqueous solution may become 1, whereby the 1,3-bis(dicarboxyphenyl)disiloxane derivative can be obtained.

Examples of the 1,3-bis(dicarboxyphenyl)-disiloxane derivatives producible by the process described above include 1,3-bis(2,2-dicarboxyphenyl)1,1,3,3-tetramethyldisiloxane, 1,3-bis(3,4-dicarboxyphenyl)-1,1,3,3-tetramethyldisiloxane, 1,3-bis(2,3-dicarboxyphenyl)-1,1,3,3-tetraphenyldisiloxane, 1,3-bis(3,4-dicarboxyphenyl)-1,1,3,3-tetraphenyldisiloxane, 1,3-bis(2,3-dicarboxyphenyl)-1,3-dimethyl-1,3-diphenyldisiloxane, 1,3-bis(3,4-dicarboxyphenyl)-1,3-dimethyl-1,3-diphenyldisiloxane, and 1-(2,3-dicarboxyphenyl)-3-(3,4-dicarboxyphenyl)-1,1,3,3-tetramethyldisiloxane.

The corresponding dianhydride can be produced from the thus obtained 1,3-bis(dicarboxyphenyl)disiloxane derivative by heating it at a temperature of 100° to 200° C. under a reduced pressure of 0.1 to 50 mmHg for a period of 2 to 10 hours or by dissolving it in acetic anhydride, refluxing the solution, and distilling off the acetic anhydride and the formed acetic acid.

When the halo-o-xylene used is a mixture of 4-halo-o-xylene and 3-halo-o-xylene, the thus produced dianhydride is a mixture of 1-(2,3-dicarboxyphenyl)-3-(3,4-dicarboxyphenyl)disiloxane derivative dianhydride and 1,3-bis(3,4-dicarboxyphenyl)disiloxane derivative dianhydride.

From this mixture, white crystals of 1,3-bis(3,4-dicarboxyphenyl)disiloxane derivative dianhydride can be obtained by separating through recrystallization from a solvent selected from the group consisting of ethers such as ethyl ether and diisopropyl ether, toluene, mixtures of toluene with ethers, and mixtures of toluene and n-hexane. Details of this separation are as follows:

In the invention, the above-said mixture of isomers comprises 1,3-bis(3,4-dicarboxyphenyl)-1,1,3,3-tetramethyldisiloxane dianhydride of formula [XII] and additionally at least one of 1-(2,3-dicarboxyphenyl)-3-(3,4-dicarboxyphenyl)-1,1,3,3-tetramethyldisiloxane dianhydride and 1,3-bis(2,3-dicarboxyphenyl)-1,1,3,3-tetramethyldisiloxane dianhydride. Such isomeric mixtures are often viscous liquids.

Upon mixing the above isomeric mixture with an ether solvent, the dianhydride of formula [XII] separates in the form of white precipitate while other isomers are dissolved in the ether.

Preferred ether solvents are diethyl ether, diisopropyl ether, and di-n-propyl ether in that the solubility of the dianhydride of formula [XII] in these ethers is low. Of these ethers, particularly preferred is diethyl ether. Such an ether is used desirably in an amount of 1 to 10 times the weight of the isomeric mixture. When the solvent is used in too small amounts, the dianhydride of formula [XII] is difficult to isolate in powder form. On the contrary, when the solvent is used in too large amounts, no fundamental problem arises but the dianhydride of formula [XII] dissolves excessively in the solvent and hence the yield tends to decrease undesirably. Suitable temperatures for the mixing are within the range of 10° C. to the reflux temperature of the solvent. When the isomeric mixture is a viscous liquid, stirring or reflux is continued until the viscous state disappears. This procedure separates only the dianhydride of formula [XII], which is hardly soluble in the ether solvent, in the form of white precipitate, which is recovered by filtration.

Further purification of the thus obtained dianhydride of formula [XII] can be accomplished by recrystallization from mixed solvents of an aromatic hydrocarbon with such an ether as mentioned above or with n-hexane.

Suitable aromatic hydrocarbons for use in the solvent mixture include benzene, toluene, and xylene, of which toluene is preferable. The proportion of aromatic hydrocarbon in the mixture thereof with the ether is desirably in the range of 10 to 80% by weight. When the proportion of aromatic hydrocarbon is too low, that is, when the proportion of ether is too high, a large amount of solvent mixture is necessary for the recrystallization since the dianhydride of formula [XII] is much less soluble in the solvent mixture of such composition. On the other hand, when the proportion of aromatic hydrocarbon is too high, the dianhydride of formula [XII] on recrystallization precipitates in a less amount since the solubility of this dianhydride is excessively high in such a solvent mixture. The aromatic hydrocarbonether mixture is used desirably in an amount of 3 to 50 times the weight of the dianhydride of formula [XII].

In the case of the solvent mixture of the aromatic hydrocarbon with n-hexane, the proportion of aromatic hydrocarbon therein is desirably in the range of 20 to 90% by weight. When the proportion of aromatic hydrocarbon is too low, that is, when the proportion of n-hexane, which is a poor solvent, is too high, a large amount of solvent mixture is necessary for the recrystallization since the dianhydride of formula [XII] is much less soluble in such a solvent mixture. When the proportion of aromatic hydrocarbon is too high, the dianhydride of formula [XII] on recrystallization precipitates in a less amount since the solubility of this dianhydride is excessively high in such a solvent mixture. The aromatic hydrocarbon-n-hexane mixture is used desirably in an amount of 3 to 50 times the weight of the dianhydride of formula [XII].

The recrystallization can be carried out according to the ordinary procedure, wherein the dianhydride of formula [XII] containing some impurities is dissolved in said solvent mixture under reflux, foreign matter is removed from the solution by hot filtration, and the filtrate is cooled or allowed to cool to precipitate crystals of the dianhydride.

The isomeric mixture stated above can also be produced in the following way.

A Grignard reagent of halo-o-xylene is coupled with a disubstituted dihalosilane represented by the general formula [I'],

wherein R and R' independently of each other denote methyl group or phenyl group, and X and X' independently of each other denote halogen. The resulting dimethylphenyldisubstitutedhalosilane isomers represented by the general formula [II'],

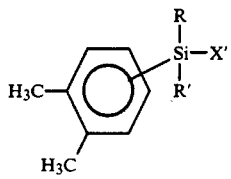

wherein X' denotes halogen and R and R' are defined above, are hydrolyzed to form 1,3-bis(dimethylphenyl)-disiloxane isomers represented by general formula [IV] given before. Thereafter, a mixture of silicon-containing tetracarboxylic dianhydride isomers represented by general formula [XI] can be produced in the same manner as stated before.

The Grignard reagent of halo-o-xylene for use in this process is prepared as described before.

Suitable disubstituteddihalosilanes include dimethyldichlorosilane, diphenyldichlorosilane methylphenyldichlorosilane and the like. Addition of such a disubstituteddihalosilane to the Grignard reagent allows the coupling reaction to proceed.

The dimethyldihalosilane is used in an amount of 0.5 to 1.5 moles per 1.0 mole of the Grignard reagent of halo-o-xylene. When the amount is less than 0.5 mole, bis(dimethylphenyl)disubstitutedsilane produces incidentally and the yield of coupling product tends to be low. When the amount exceeds 1.5 moles, the excess of the disubstituted dihalosilane converts eventually into polysiloxane compounds, which are liable to contaminate the intermediate compound of the general formula [VI] during its production, though this contaminant can be removed by distillation.

For the purpose of offsetting this disadvantage, the disubstituted halosilane is used in an amount preferably from 0.9 to 1.1 moles, most desirably from 0.95 to 1.0 mole, per 1.0 mole of the Grignard reagent of halo-o-xylene.

The coupling reaction is carried out at a temperature desirably from 0° to 60° C. for a period generally from 1 to 5 hours. When the reaction temperature is low, the reaction period is prolonged but no fundamental problem arises. On the contrary, when the reaction at higher temperatures than 60° C. tends to yield much by-products including polysiloxane compounds and other high-boiling compounds and bis(dimethylphenyl)-disubstitutedsilane.

After completion of the coupling reaction, water is added in an amount at least 1 mole to 1 mole of the formed dimethylphenyldisubstitutedhalosilane represented by the general formula [II'] which has been either taken out from the reactor or retained as such without taking out, whereby this compound can be converted into 1,3-bis(dimethylphenyl)disiloxane derivative represented by the general formula [IV]. In this case, water is added desirably in a large excess over the dimethylphenyldisubstitutedhalosilane. This is for the purpose of facilitating the separation of an aqueous layer in which magnesium halide formed by the the coupling reaction is dissolved, from an organic layer, both layers being formed by adding water. This reaction can be completed by stirring generally at a temperature of 10° to 50° C. for a period of 10 minutes to 1 hour. For instance, the reaction proceeds sufficiently at room temperature.

After completion of this reaction, the separated organic layer comprising ethyl ether, tetrahydrofuran, or the like as a solvent washed with water to remove magnesium halide completely, and is distilled, if necessary, to purify 1,3-bis(dimethylphenyl)disiloxane derivative represented by the general formula [IV].

1,3-bis(dicarboxyphenyl)disiloxane derivatives and dianhydride thereof produced according to the present invention are useful as raw materials of polyimide resins and of other resins, as hardeners for epoxy resins, and as others.

EXAMPLE 1

(1) Preparation of Grignard reagent

After being dried sufficiently with argon gas, a 2-liter, 4-necked flask equipped with an Allihn condenser, dropping funnel, thermometer, and stirrer was charged with 100 ml of tetrahydrofuran dehydrated with metallic sodium, 9.72 g of metallic magnesium, and 10.0 g of bromo-o-xylene (a mixture of 4-bromo-o-xylene and 3-bromo-o-xylene in 75:25 ratio). Over 1 hour from the time this reaction liquid began to cloud indicating the start of Gregnard reagent formation, a mixture of 64.0 g of the same bromo-o-xylene as stated above and 100 ml of tetrahydrofuran was added dropwise from the dropping funnel. During this dropping, the reaction temperature was kept at 40° C. by cooling with an ice-bath, since this reaction is exothermic. After the dropping had been finished, the reaction mixture, in which metallic magnesium remained still, was heated with stirring on an oil bath at 40° C. for 5 hours to convert metallic magnesium completely to the Grignard reagent.

(2) Coupling reaction

To the resulting mixture was added dropwise 37.85 g (0.40 mole) of dimethylchlorosilane in 20 minutes. The reaction temperature was kept at 40° C. during this dropping and then at 20° C. for 5 hours to complete the coupling reaction.

Then, 100 ml of water deionized by ion exchange was added gradually to dissolve the chlorobromomagnesium formed by the coupling reaction. The contents of the flask separated into the upper layer, a dimethylphenyldimethylsilane-containing tetrahydrofuran solution, and the lower layer, an aqueous solution. The lower layer was removed, and the upper layer was washed 4 times with 50 ml each of water deionized by ion exchange, and was dehydrated over anhydrous sodium sulfate.

(3) Hydroxylation

All the dehydrated tetrahydrofuran solution containing dimethylphenyldimethylsilane was placed in a 1-liter flask equipped with an Allihn condenser, thermometer, and stirrer, and 20 ml of water deionized by ion exchange and 0.3 g of a 5 wt % palladium-on-active carbon catalyst (the quantity of metallic palladium: 0.023 wt % of dimethylphenyldimethylsilane) were added with stirring at room temperature: 23° C. Then, hydrogen gas began evolving immediately. Measurement with a wet type of gas meter attached to the outlet of the Allihn condenser indicated that 9.75 l (0.394 mole) at 23° C. of hydrogen gas evolved until the evolution ceased 2.5 hours after the initiation of reaction. The reaction product mixture was filtered to remove the palladium catalyst, and also the lower aqueous layer was removed, giving a tetrahydrofuran solution of dimethylphenyldimethylhydroxysilane.

(4) Dehydration-condensation

All the tetrahydrofuran solution of dimethylphenyldimethylhydroxysilane obtained was placed in a 1-liter flask equipped with an Allihn condenser, thermometer, and stirrer. Then, 15 ml of 36% hydrochloric acid was added with stirring at 20° C. to initiate reaction, which was continued for 8 hours to completion. The resulting lower aqueous layer containing hydrochloric acid was removed by means of a separating funnel, and 100 ml of toluene was added to the separated tetrahydrofuran solution of 1,3-bis(dimethylphenyl)-1,1,3,3-tetramethyldisiloxane. The resulting solution was washed three times with 70 ml each of water deionized by ion exchange, and the tetrahydrofuran and toluene were distilled off from the washed solution, giving 66.8 g (0.195 mole) of raw 1,3-bis(dimethylphenyl)-1,1,3,3-tetramethyldisiloxane.

Analysis by gel permeation chromatography indicated that this product was composed of 98 wt % of 1,3-bis(dimethylphenyl)-1,1,3,3-tetramethyldisiloxane, 1.5 wt % of presumable polysiloxane compounds, and 0.5 wt % of the unreacted hydroxysilane compound.

This liquid was rectified by using a still provided with a Vigreaux column, giving 62.1 g of a fraction, b.p. 141°-144° C. (at 0.52 mmHg). This fraction was identified by proton NMR analysis as 1,3-bis-(dimethylphenyl)-1,1,3,3-tetramethyldisiloxane.

(5) Oxidation

Then, 13.7 g (40 m moles) of the rectified 1,3-bis(-dimethylphenyl)-1,1,3,3-tetramethyldisiloxane, 240 ml of pyridine, and 120 ml of water deionized by ion exchange were placed in a 1-liter, 4-necked flask equipped with an Allihn condenser, thermometer, and stirrer. After heating of the flask contents to 85° C., 75.9 g (480 m moles) of potassium permanganate was added gradually over 2 hours under stirring and the resulting mixture was further stirred at 85° C. for 4 hours. A precipitate of manganese oxide formed by the reaction was filtered off, and the pyridine was removed from the filtrate by evaporation using a rotary evaporator. Upon addition of 36% hydrochloric acid to the residual aqueous solution, a white resinous precipitate appeared. At this time the aqueous solution showed pH 1. The precipitate was dissolved in a mixture of 220 ml of tetrahydrofuran and 150 ml of toluene and the solution was washed 4 times with 75 ml each of 10% brine. The solvent was removed from the washed solution by evaporation using a rotary evaporator, giving 17.4 g of a pale yellow-brown resinous tetracarboxylic acid.

(6) Dehydration ring closure

Then, 13.9 g (30 m moles) of the above resinous tetracarboxylic acid, placed in a 100-ml eggplant-shaped flask, was subjected to dehydration ring closure by heating at 150° C. for 3 hours under a reduced pressure of 0.7 mmHg. The obtained dianhydride was resinous and the yield was 12.4 g (29 m moles).

This product was confirmed to be an hydride from the result of proton NMR analysis that no absorption by the proton of carboxylic acid was observed in weak magnetic fields of 10 to 13 ppm and from the result of IR analysis that no absorption by the hydroxy group was observed.

The obtained dianhydride was a mixture containing 1-(2,3-dicarboxyphenyl)-3-(3,4-dicarboxyphenyl)-1,1,3,3-tetramethyldisiloxane dianhydride and 1,3-bis-(3,4-dicarboxyphenyl)-1,1,3,3-tetramethyldisiloxane dianhydride as main components and a trace of 1,3-bis-(2,3-dicarboxyphenyl)-1,1,3,3-tetramethyldisiloxane dianhydride.

(7) Separation and purification

To 10.0 g of the above resinous dianhydride contained in a 100-ml eggplant-shaped flask, 20 g of ethyl ether and 10 g of toluene were added and refluxed by heating to dissolve the dianhydride. The solution was hot-filtered, and on cooling the filtrate, white crystals of 1,3-bis(3,4-dicarboxyphenyl)-1,1,3,3-tetramethyldisiloxane dianhydride precipitated. These crystals were filtered and dried, yield 4.8 g, m.p. 136°-138° C. This m.p. value is in agreement with that of 1,3-bis(3,4-dicarboxyphenyl)-1,1,3,3-tetramethyldisiloxane dianhydride which is reported in J. Org. Chem. Vol. 38, p. 4271 (1973).

1,3-Bis(dimethylphenyl)-1,1,3,3-tetramethyldisiloxane rectified in the above hydrolysis step (4) was analyzed by proton NMR spectrometry.

From the result of this analysis, the above disiloxane derivative was found to be a mixture of the following three isomers:

1,3-Bis(3,4-dimethylphenyl)-1,1,3,3-tetramethyldisiloxane

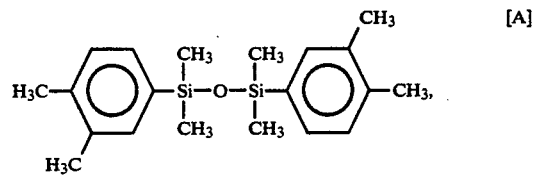

1-(2,3-dimethylphenyl)-3-(3,4-dimethylphenyl)-1,1,3,3-tetramethyldisiloxane

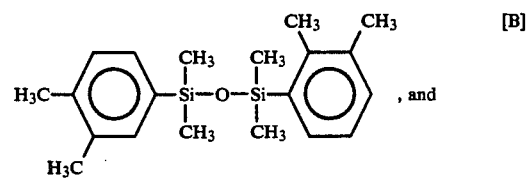

1,3-bis(2,3-dimethylphenyl)-1,1,3,3-tetramethyldisiloxane

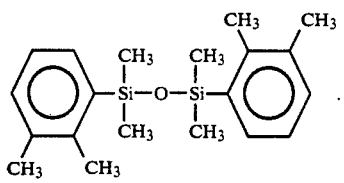

The proton NMR spectrum showed absorption maxima at 0.31 ppm due to the protons of the methyl groups attached to the silicon atoms of compound [A], at 0.38 ppm due to the protons of the methyl groups attached to the 1-positioned silicon atom of compound [B], at 0.33 ppm due to the protons of the methyl groups attached to the 3-positioned silicon atom of compound [B], and at 0.39 ppm due to the protons of the methyl groups attached to the silicon atoms of compound [C]. The relative integrated intensities of these absorption bands were 13.0:3.5:3.5:1 in the above order. Accordingly, the 1,3-bis(dimethylphenyl)-1,1,3,3-tetramethyldisiloxane rectified in the hydrolysis step (4) was found to be a mixture of 62% [13.0/(13.0+3.5+3.5+1)] of compound [A], 33% [(3.5+3.5)/(13.0+3.5+3.5+1)] of compound [B], and 5% [1/(13.0+3.5+3.5+1)] of compound [C].

Reflecting these proportions, the above 1,3-bis(dicarboxyphenyl)-1,1,3,3-tetramethyldisiloxane dianhydride derived from the disiloxane derivative of the step (4) by oxidation and dehydration ring closure was an isomeric mixture of 62 wt% of 1,3-bis(3,4-dicarboxyphenyl)-1,1,3,3-tetramethyldisiloxane dianhydride, 33 wt % of 1-(2,3-dicarboxyphenyl)-3-(3,4-dicarboxyphenyl)-1,1,3,3-tetramethyldisiloxane dianhydride, and 5 wt % of 1,3-bis(2,3-dicarboxyphenyl)-1,1,3,3-tetramethyldisiloxane dianhydride.

EXAMPLE 2

10 Gram of the isomeric dianhydride mixture obtained by the dehydration ring closure in step (6) of Example 1 was heated together with 25 ml (17.9 g) of diethyl ether under reflux for 4 hours in a 100-ml eggplant-shaped flask. Upon allowing this mixture to cool, a white precipitate appeared. This precipitate was filtered and dried, giving 5.2 g of a white powder. Proton NMR analysis of this powder showed a sharp absorption at 0.46 ppm due to the protons of the methyl groups attached to the silicon atoms. Because the presence of only one absorption maximum means the equivalence of the methyl groups attached to the silicon atoms, the white powder obtained can be confirmed to consist essentially of 1,3-bis(3,4-dicarboxyphenyl)-1,1,3,3-tetramethyldisiloxane dianhydride. In addition, the powder was identified as an anhydride since no absorption due to the proton of a carboxy group was observed between 10 and 13 ppm. The ratio of the integrated absorbance (a) ranging from 8.05 to 8.17 ppm to the integrated absorbance (b) around 0.46 ppm was 1.0:2.0, the absorbance (a) being assigned to the protons attached to the benzene rings and the absorbance (b) being assigned to the protons of the methyl groups attached to the silicon atoms. These results also reflect the structure of this white powdery compound.

The melting point of the white powder obtained was 127°–133° C. The powder purity presumed from this melting point value raises no problem associated with NMR spectra. However, this melting point is considerably lower than the literature value of 137°–138° C. Therefore, this powder was subjected to the following recrystallization treatment.

10 Gram of this isomeric mixture was heated together with 25 ml (17.9 g) of diethyl ether under reflux for 4 hours in a 100-ml eggplant-shaped flask. Upon allowing this mixture to cool, a white precipitate appeared. This precipitate was filtered and dried, giving 5.2 g of a powder.

Further, this white powder was recrystallized in a solvent mixture of 25 ml of diethyl ether and 25 ml of toluene, yielding 4.2 g of white crystals, m.p. 137°–138° C. This melting point is in agreement with the value reported in J. Org. Chem., Vol. 28, p. 4271. From the results of $^{13}C$-NMR analysis and proton NMR analysis, this compound was identified as 1,3-bis(3,4-dicarboxyphenyl)-1,1,3,3-tetramethyldisiloxane dianhydride.

EXAMPLE 3

1.0 Gram of the white powder melting at 127°–133° C. purified roughly in Example 2 by using diethyl ether was recrystallized in a solvent mixture of 20 ml of toluene and 10 ml of n-hexane, giving 0.84 g of acicular crystals, m.p. 136°–137° C.

Effect of the invention

According to the present invention, intended 1,3-bis(dicarboxyphenyl)disiloxane derivatives and dianhydrides thereof can be produced with good productivity and in high yields.

What is claim is:

1. A process for producing 1,3-bis(3,4-dicarboxyphenyl)-1,1,3,3-tetramethyldisiloxane dianhydride of formula XII

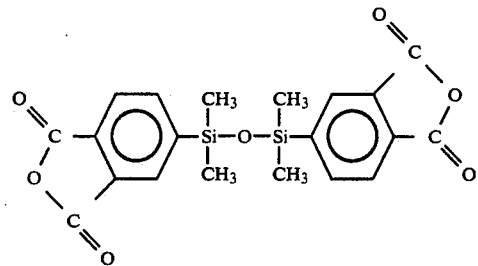

comprising mixing a mixed solvent of an aromatic hydrocarbon and an ether solvent with a mixture of silicon-containing tetracarboxylic dianhydride isomers represented by the general formula XI

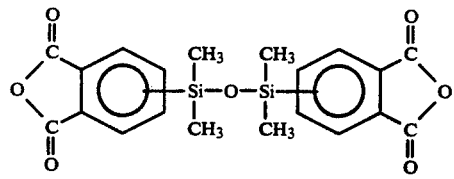

forming a precipitate of the 1,3-bis(3,4-dicarboxyphenyl)-1,1,-3,3-tetramethyldisiloxane dianhydride of formula XII and recovering the formed precipitate to yield the intended product in the form of white powder.

2. A process for producing 1,3-bis(3,4-carboxyphenyl) -1,1,3,3-tetramethyldisiloxane dianhydride from a mixture of bis(dicarboxyphenyl)-tetramethyldisiloxane dianhydride isomers represented by the general formula XI

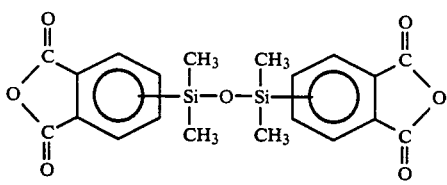

containing 1,3-bis(3,4-dicarboxyphenyl)-1,1,3,3-tetramethyldisiloxane dianhydride of formula XII

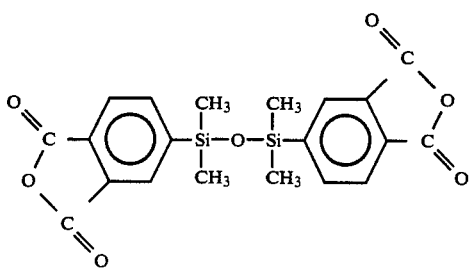

and additionally at least one of 1,(2,3-dicarboxyphenyl)-3-(3,4-dicarboxyphenyl)-1,1,2,2-tetramethyldisiloxane dianhydride and 1,3-bis(2,3-dicarboxyphenyl)-1,1,3,3-tetramethyldisiloxane dianhydride through recrystallization;

which comprises mixing a mixed solvent of an aromatic hydrocarbon and an ether solvent with the mixture of bis(dicarboxyphenyl)-tetramethyldisiloxane dianhydride isomers in an amount of 3 to 50 times the weight of the dianhydride of formula XII; heating and then cooling the above mixture to form precipitates of 1,3-bis(3,4-dicarboxyphenyl)-1,1,3,3-tetramethyldisiloxane dianhydride of formula XII and collecting the precipitates by filtration to yield the 1,3-bis(3,4-dicarboxyphenyl)-1,1,3,3-tetramethyldisiloxane dianhydride of formula XII in the form of white powder.

3. The process of claim 2, wherein the proportion of the aromatic hydrocarbon in the mixture thereof with the ether is in the range of 10 to 80% by weight.

4. The process of claim 3, wherein the aromatic hydrocarbon is selected from the group consisting of benzene, toluene and xylene and the ether is selected from the group of diethyl ether, diisopropyl ether and di-n-propyl ether.

5. The process of claim 1, wherein the mixture of bis(dicarboxyphenyl)-tetramethyldisiloxane dianhydride isomers is heated under reflux to dissolve the dianhydride of formula XII, foreign matter is removed from the resulting solution by hot filtration and the filtrate is cooled or allowed to cool to form said precipitates of said 1,3-bis(3,4-dicarboxyphenyl)-1,-1,3,3-tetramethyldisiloxane dianydride of formula XII.

6. The process of claim 4, wherein the mixture of bis(dicarboxyphenyl)-tetramethyldisiloxane dianhydride isomers is heated under reflux to dissolve the dianhydride of formula XII, foreign matter is removed from the resulting solution by hot filtration and the filtrate is cooled or allowed to cool to form said precipitates of said 1,3-bis(3,4-dicarboxyphenyl)-1-1,3,3-tetramethyldisiloxane dianhydride of formula XII.

7. The process of claim 1 wherein the proportion of the aromatic hydrocarbon in the mixture thereof with the ether solvent is in the range of 10 to 80% by weight.

8. The process of claim 7, wherein the aromatic hydrocarbon is selected from the group consisting of benzene, toluene and xylene and the ether solvent is selected from the group consisting of diethyl ether, diisopropyl ether, and di-n-propyl ether.

* * * * *